United States Patent
Hasumi

(10) Patent No.: US 8,961,957 B2
(45) Date of Patent: Feb. 24, 2015

(54) THERAPY AND METHOD FOR INTRATUMORALLY INTRODUCING CYTOTOXIC T LYMPHOCYTE AND/OR NKT CELL WITH ANTI-TNF AND/OR ANTI-IL-10

(71) Applicant: Hasumi International Research Foundation, Washington, DC (US)

(72) Inventor: Kenichiro Hasumi, Suginami-Ku Tokyo (JP)

(73) Assignee: Hasumi International Research Foundation, Washington, DC (US)

( * ) Notice: Subject to any disclaimer, the term of this patent is extended or adjusted under 35 U.S.C. 154(b) by 0 days.

(21) Appl. No.: 13/928,844

(22) Filed: Jun. 27, 2013

(65) Prior Publication Data

US 2014/0004126 A1 Jan. 2, 2014

Related U.S. Application Data

(60) Provisional application No. 61/664,998, filed on Jun. 27, 2012.

(51) Int. Cl.
| | | |
|---|---|---|
| *A01N 63/00* | (2006.01) | |
| *A61K 45/00* | (2006.01) | |
| *A61K 47/00* | (2006.01) | |
| *A61K 39/395* | (2006.01) | |
| *C12N 5/0786* | (2010.01) | |
| *C12N 5/0783* | (2010.01) | |
| *C07K 16/24* | (2006.01) | |

(52) U.S. Cl.
CPC ............. *A61K 39/3955* (2013.01); *A61K 35/15* (2013.01); *A61K 35/17* (2013.01); *C12N 5/0645* (2013.01); *C12N 5/0638* (2013.01); *C12N 5/0646* (2013.01); *C07K 16/241* (2013.01)

USPC .................................... 424/93.71; 424/278.1

(58) Field of Classification Search
None
See application file for complete search history.

(56) References Cited

U.S. PATENT DOCUMENTS

| | | | |
|---|---|---|---|
| 2005/0123522 A1 | 6/2005 | Punnonen et al. | |
| 2006/0057120 A1 | 3/2006 | Bosch | |
| 2008/0160050 A1* | 7/2008 | Hasumi | 424/277.1 |
| 2009/0148452 A1* | 6/2009 | Wakkach et al. | 424/139.1 |
| 2010/0203010 A1 | 8/2010 | Hariharan et al. | |
| 2011/0135617 A1 | 6/2011 | Kruse | |

OTHER PUBLICATIONS

Baker et al., 2001, Blood. vol. 97: 2923-31.*
Gelbard et al. "Combination Chemotherapy and Radiation of Human Squamous Cell Carcinoma of the Head and Neck Augments CTL-Mediated Lysis." Clin. Cancer Res 12:1897-1905. May 3, 2007.
Hasumi et al. "Therapeutic Response in Patients with Advanced Malignacies Treated with Combined Dendritic Cell-Activated T Cell Based Immunotherapy and Intensity-Modulated Radiotherapy." Cancer (Basel) 3(2): 2223-42. Apr. 28, 2011.

* cited by examiner

*Primary Examiner* — Amy Juedes
(74) *Attorney, Agent, or Firm* — Eckert Seamans Cherin & Mellott, LLC; Carol A. Marmo

(57) ABSTRACT

The invention relates to therapy and methods of applying the therapy to cancer patients. The invention includes introducing intratumorally cytotoxic T lymphocyte and/or NKT cells, and prior to, coincident with, or following introducing intratumorally the cytotoxic T lymphocyte and/or NKT cells, introducing intratumorally anti-TNF and/or anti-IL-10 to the patient. The cytotoxic T lymphocyte and/or NKT cells can be induced by the intratumoral introduction of immature dendritic cells to the patient. This therapy of the invention can be effective to regress, reduce or eliminate tumor cells in tumor tissue of the patients in the absence of radiation therapy.

15 Claims, 4 Drawing Sheets

THERAPY AND METHOD FOR INTRATUMORALLY INTRODUCING CYTOTOXIC T LYMPHOCYTE AND/OR NKT CELL WITH ANTI-TNF AND/OR ANTI-IL-10

CROSS-REFERENCE TO RELATED APPLICATIONS

This application claims priority under 35 U.S.C. Section 119(e) from Provisional Application 61/664,998, entitled "Therapy and Method for Intratumorally Introducing Cytotoxic T Lymphocyte and/or NKT Cell With Anti-TNF and/or Anti-IL-10" filed on Jun. 27, 2012.

FIELD OF THE INVENTION

The invention relates to intratumoral therapy and methods for applying the therapy to treat a cancer patient. The invention includes introducing cytotoxic T lymphocyte and/or natural killer T (NKT) cells with anti-tumor necrosis factor (anti-TNF) and/or anti-IL-10 into tumor tissue of a patient.

DESCRIPTION OF THE PRIOR ART

Cytotoxic T lymphocytes are an important component of cellular immunity. They play a critical role in the control of many infections and cancers. These T cells are responsible for "hunting down" other cells of the body that are infected by viruses or are cancer-containing, and destroying them. For example, when a virus or cancer is using a cell to reproduce, the cell displays some of the viral proteins or cancer components on its surface. The cytotoxic T cells can recognize these proteins or components and hone-in to destroy the infected or cancer-containing cells before they can release the new infection or cancer into the bloodstream. Many vaccines are effective, at least in part, by stimulating this type of T cell activation or response. Cytotoxic cells can also create chemicals known as cytokines which assist in coordinating how the immune system fights against disease.

NKT cells represent a heterogeneous group of T cells that share properties of both T cells and natural killer cells.

Tumor necrosis factor (TNF) is a cytokine which circulates throughout the body, TNF is critical for effective immune surveillance and is required for proper proliferation and function of natural killer cells, T cells, B cells, macrophages, and dendritic cells. The primary role of TNF is in the regulation of immune cells. It is known that TNF can cause systemic inflammation which can result in various chronic conditions. Anti-TNF, also known as TNF blockers or inhibitors, interfere with the body's production of TNF.

There is a need in the art to develop therapy and methods of applying said therapy to regress, reduce or eliminate tumor cells in tumor tissue of patients. It is desirable for the therapy and methods of application to be effective in a reasonable period of time and it would be further desirable for the therapy and methods of application to be as minimally invasive to the patients as reasonably possible. Further, it is advantageous if the therapy and methods are successful in the absence of subjecting the patient to radiation therapy.

SUMMARY OF THE INVENTION

The invention solves the above need by providing effective therapy and methods for regression, reduction or elimination of tumor cells in local tumor tissue of a patient and tumor cells in metastasized tumors. In one aspect, the invention provides a method which includes collecting monocyte cells from a patient, culturing the monocyte cells to form immature dendritic cells, introducing intratumorally a therapeutically effective amount of immature dendritic cells to the patient, collecting cytotoxic T lymphocyte and/or NKT cells from the patient, introducing intratumorally a therapeutically effective amount of the cytotoxic T lymphocyte and/or NKT cells to the patient, and introducing intratumorally a therapeutically effective amount of anti-TNF and/or anti-IL-10 to the patient.

The cytotoxic T lymphocyte and/or NKT cells can be cultured in a medium including IL-2 and CD3.

Introducing intratumorally the anti-TNF and/or anti-IL-10 can be prior to or following or coincident with introducing intratumorally the cytotoxic T lymphocyte and/or NKT cells.

The method can further include administering to the patient a treatment selected from the group consisting of chemotherapy, radiotherapy, antibody therapy, and combinations thereof.

In another aspect, the invention provides a method including intratumorally introducing a therapeutically effective amount of immature dendritic cells to the tumor tissue, intratumorally introducing a therapeutically effective amount of cytotoxic T lymphocyte and/or NKT cells to the tumor tissue, and intratumorally introducing a therapeutically effective amount of anti-TNF and/or anti-IL-10 to the tumor tissue.

The therapeutically effective amount of cytotoxic T lymphocyte and/or NKT cells can be induced by the introduction of the immature dendritic cells.

BRIEF DESCRIPTION OF THE DRAWINGS

A further understanding of the invention can be gained from the following description of the preferred embodiments when read in conjunction with the accompanying drawings in which.

DETAILED DESCRIPTION OF PREFERRED EMBODIMENTS

Figure 1:
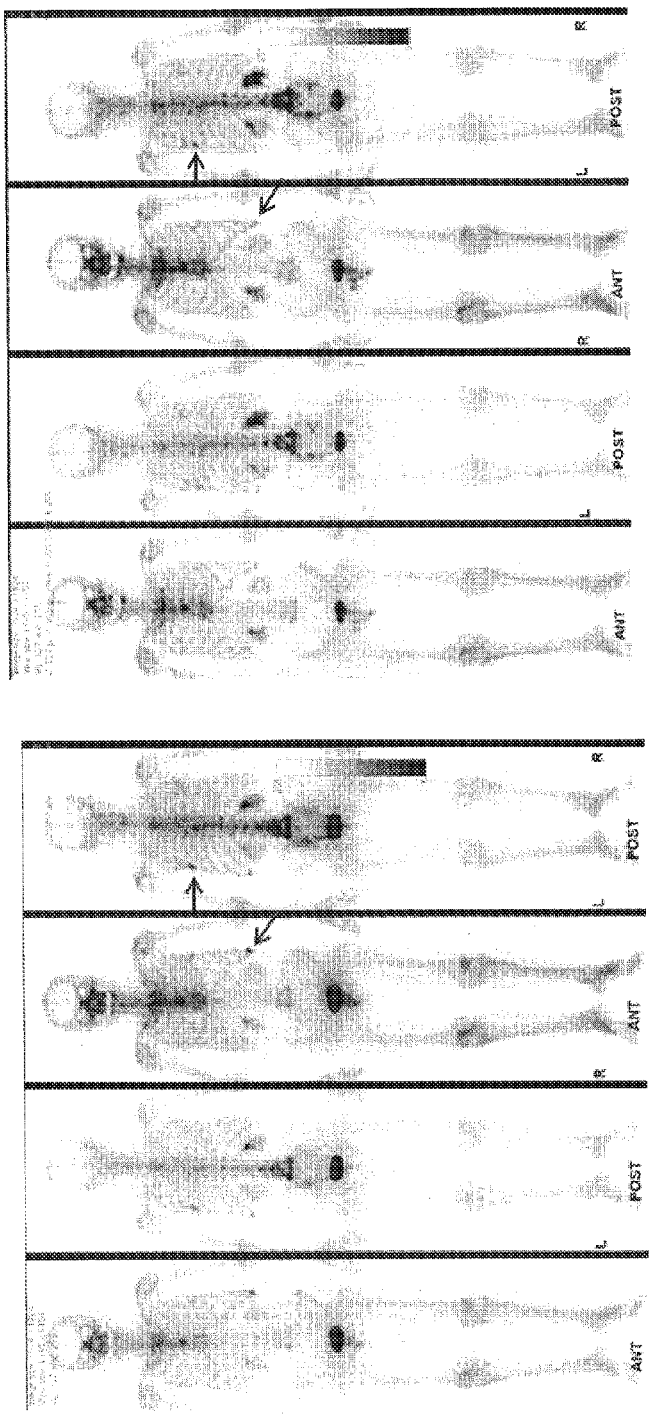
FIG. 1 is a radioisotope image of lt. ribs 7 and 10 showing tumor tissue before and after therapy, in accordance with one embodiment of this invention.

As used herein, "patient(s)" include mammal(s), which include human(s).

As used herein, the term "therapeutically effective amount" refers to that amount of cytotoxic T lymphocyte cells, NKT cells, anti-TNF, anti-IL-10, immature dendritic cells, anti-inflammatory agent, adjuvant, chemotherapy, radiotherapy, antibody therapy, or combinations thereof, required to bring about a desired effect in a human or other mammal. In all instances, at its most basic level, the desired effect is a regression, reduction or elimination of tumor cells in tumor tissue of the patient when compared to the tumor cells in the tumor tissue of the patient prior to employing the therapy methods of the invention.

As used herein, the term "intratumoral therapy" refers to therapy that includes the introduction (e.g., injection) of cytotoxic T lymphocyte and/or NKT cells with anti-TNF and/or anti-IL-10, and optionally an anti-inflammatory agent, and/or immature dendritic cells and optionally an adjuvant, directly into the tumor tissue of a patient (a human or an animal). The anti-TNF and/or anti-IL-10 can be intratumorally introduced prior to, coincident with, or following intratumorally introducing the cytotoxic T lymphocyte and/or NKT cells. Further, the cytotoxic T lymphocyte and/or NKT cells can be optionally introduced in conjunction with an anti-inflammatory agent, and the immature dendritic cells can be optionally introduced in conjunction with an adjuvant. The combination of the cytotoxic T lymphocyte and/or NKT cells with the anti-TNF and/or anti-IL-10, and the optional compounds identified, within the tumor tissue is effective to regress, reduce and/or eliminate tumor cells.

In general, the invention relates to combining immature dendritic cells, cytotoxic T lymphoctye and/or NKT cells with anti-TNF and/or anti-IL-10 and intratumorally (e.g., directly) introducing into tumor tissue, including tumor tissue formed by metastasis, of a patient.

Without intending to be bound by any particular theory, it is believed that the intratumoral injection of immature dendritic cells into the patient results in the inducement of cytotoxic T lymphocyte and/or NKT cells. That is, cytotoxic T lymphocyte and/or NKT cells are induced as part of an immunoresponse caused by the intratumoral injection of immature dendritic cells. Such immunoresponse may promote a TNF response, which may in turn induce inflammation at the tumor site and progress the growth of the tumor. Thus, the anti-TNF and/or anti-IL-10 can be combined (e.g., co-introduced or co-injected) with the cytotoxic T lymphocyte and/or NKT cells to inhibit such inflammation.

Further, without intending to be bound by any particular theory, it is believed that the cytotoxic T lymphocyte and/or NKT cells naturally induced as part of the autoimmune response as above-described, may not be potent against tumors especially when the tumors are at an advanced stage or aggressively growing. The reasons may be that these cytotoxic T lymphocyte and/or NKT cells are not induced in an adequate quality and/or in an adequate quantity and/or in a timely manner to defend the patient's body from the tumor invasion. It has been found that the intratumoral injection of immature dendritic cells can positively promote the immunoresponse to induce cytotoxic T lymphocyte and/or NKT cells having improved quality, increased quantity and timely manner. However, in addition to promoting the immunoresponse, intratumoral injection of the immature dendritic cells can also induce the TNF level in the patient's bloodstream and increase inflammation at the tumor site(s) which can interfere with the immunoresponse of the cytotoxic lymphocyte and/or NKT cells.

Anti-TNF antibody is effective to suppress the systemic inflammation caused by TNF and by suppressing the inflammation, the cytotoxic T lymphocyte and/or NKT cells are not limited in their immunological function.

Thus, it is an object of the invention to provide an adequate quantity and quality of cytotoxic T lymphocyte and/or NKT cells in the patient's body and particularly at the tumor site(s) to regress, reduce or eliminate tumor cells. Further, these cells are combined with anti-TNF and/or anti-IL-10 to inhibit potential inflammation at the tumor site(s). It is contemplated that the quantity and quality of the natural cytotoxic T lymphocyte and/or NKT cells (i.e., induced by the intratumoral introduction of immature dendritic cells into the patient) may be sufficient (e.g., a therapeutically effective amount) to accomplish this objective. However, it is also contemplated that the quantity and quality of the natural cytotoxic T lymphocyte and/or NKT cells may not be sufficient and therefore, the invention provides for collecting the natural cytotoxic T lymphocyte and/or NKT cells from the patient, optionally culturing these collected cells, and re-introducing them in combination with anti-TNF and/or anti-IL-10 intratumorally into the patient in a quantity and quality which is sufficient (e.g., a therapeutically effective amount) to regress, reduce or eliminate tumor cells and to inhibit inflammation at the tumor site(s).

In general, the anti-TNF antibody is introduced when there is a sufficient amount of cytotoxic T lymphocyte presenting in the autoimmune system of the patient, such that the immune response of the cytotoxic T lymphocyte is supported by suppressing the activity of the TNF.

The anti-TNF antibody can be in various forms. For example, the anti-TNF antibody can be incorporated into a delivery mechanism, such as a liquid carrier or medium, to facilitate introduction (e.g., injection).

Thus, in certain embodiments, the invention includes collecting monocyte cells from a patient, culturing the collected monocyte cells in a suitable medium to form immature dendritic cells, and introducing intratumorally a therapeutically effective amount of the immature dendritic cells into the patient. Further, following the intratumoral introduction of the immature dendritic cells, cytotoxic T lymphocyte and/or NKT cells are collected from the patient, cultured in a suitable medium and combined with anti-TNF and/or anti-IL-10 for intratumoral introduction in a therapeutically effective amount into the patient. The anti-TNF and/or anti-IL-10 can be intratumorally introduced prior to, coincident with, or following introducing intratumorally the cultured cytotoxic T lymphocyte and/or NKT cells. The invention is effective to cause regression, reduction or elimination of tumor cells in a patient. Furthermore, in certain embodiments, this can be accomplished in the absence of radiation therapy.

As stated herein, the invention includes the combination of cytotoxic T lymphocyte and/or NKT cells with anti-TNF and/or anti-IL-10 in tumor tissue. In certain embodiments, the cytotoxic T lymphocyte includes CD8+NK T cell population. The cytotoxic T lymphocyte and NKT cells are produced by the patient and can be re-introduced into the same patient. Similarly, the monocyte cells are produced by the patient and are re-introduced as immature dendritic cells into the same patient. In certain embodiments, the intratumoral introduction of the dendritic cells, cytotoxic T lymphocyte and/or NKT cells, and anti-TNF and/or anti-IL-10 is carried out by injection into the patient.

In certain embodiments, the invention is a human-initiated therapeutic vaccine with cytotoxic T lymphocyte and/or NKT cells in combination with anti-TNF and/or anti-IL-10.

The cytotoxic T lymphocyte and/or NKT cells collected from the patient can be cultured in a medium selected from those which are known in the art. In certain embodiments, the medium includes IL-2, CD3, or mixtures thereof.

In certain embodiments, the cytotoxic T lymphocyte and/or NKT cells can be introduced to the patient in conjunction with an anti-inflammatory agent. Suitable anti-inflammatory agents can include those that are known in the art. The cytotoxic T lymphocyte and/or NKT cells, and anti-inflammatory agent can be combined to form a composition and the composition can be introduced intratumorally into the patient.

In certain embodiments, the invention can optionally include a precursor treatment. Prior to introducing (e.g., collecting and culturing the cytotoxic T lymphocyte and/or NKT cells and re-introducing), intratumorally the cytotoxic T lymphocyte and/or NKT cells to the patient, the patient can be administered a treatment selected from chemotherapy, radiotherapy, antibody therapy, and combinations thereof. Chemotherapy, radiotherapy and antibody therapy regimens are well known in the art and these known regimens are suitable for use in the invention.

Optionally, it is contemplated that the use of chemotherapy, radiotherapy, antibody therapy, and combinations thereof can be employed at various other times throughout the method of the invention.

Further, in certain embodiments, it is contemplated that the therapy of the invention does not include the use of radiation therapy. Thus, the therapy of the invention can be effective to regress, reduce, or eliminate tumor tissue in a patient in the absence of radiation therapy.

In certain embodiments, the invention can include the treatment steps of; intratumorally introducing immature dendritic cells in a therapeutically effective amount into the tumor tissue of the patient; collecting from the patient cytotoxic T lymphocyte and/or NKT cells induced by the introduction of the immature dendritic cells; re-introducing the collected cytotoxic T lymphocyte and/or NKT cells into the tumor tissue of the same patient; and introducing intratumorally anti-TNF and/or anti-IL-10 into the patient. The intratumoral introduction of the immature dendritic cells is a prerequisite to the intratumoral introduction of the cytotoxic T lympohocyte and/or NKT cells with the anti-TNF and/or anti-IL-10 for inducement of the natural cytotoxic T lymphocyte and/or NKT cells.

In certain embodiments, the inducement of cytotoxic T lymphocyte and/or NKT cells by the immature dendritic cells is sufficient (e.g., a therapeutically effective amount) such that the natural cytotoxic T lymphocyte and/or NKT cells are not removed from the patient and not re-introduced. Thus, the anti-TNF and/or anti-IL-10 can be introduced intratumorally to inhibit inflammation in the absence of the intratumoral introduction of cytotoxic T lymphocyte and/or NKT cells. That is, the intratumoral introduction of immature dendritic cells can be in combination with the intratumoral introduction of the anti-TNF and/or anti-IL-10.

In certain embodiments, the invention can include the treatment steps of: intratumorally introducing immature dendritic cells in a therapeutically effective amount into the tumor tissue of the patient; inducing a therapeutically effective amount of cytotoxic T lymphocyte and/or NKT cells in the tumor tissue of the patient; and introducing intratumorally anti-TNF and/or anti-IL-10 into the patient. The intratumoral introduction of the immature dendritic cells is a prerequisite to the inducement of the cytotoxic T lympohocyte and/or NKT cells and the intratumoral introduction of the anti-TNF and/or anti-IL-10.

The monocyte cells collected from the patient are cultured in a medium, such as but not limited to, IL-4 and GM-CFS. The immature dendritic cells are introduced intratumorally into the patient. In certain embodiments, the immature dendritic cells can be introduced in conjunction with an adjuvant. The immature dendritic cells and the adjuvant can be combined to form a composition and the composition can be introduced intratumorally into the patient.

Suitable adjuvants for use in the invention can include, without limitation, lipid-based, protein-based and polysaccharides-based adjuvants, such as lymphocyte cultured medium, Marignase, Agaricus, OK432, BCG, Lentinan (shii-take), Reishi, Sarunokoshikake, TNF Meshimakobu, Froint's complete or incomplete adjuvant. LPS, fatty acids, TW80, phospholipids, cytokines or a virus. In certain embodiments, the adjuvant can be a leukocyte cultured medium (LCM) adjuvant. The LCM adjuvant can include at least three cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα and VEGF.

In certain embodiments, the therapy of the invention includes the following steps:

Step 1: Collecting monocyte cells from a patient;

Step 2: Culturing the monocyte cells collected from the patient to form immature dendritic cells;

Step 3: Intratumorally introducing the immature dendritic cells to the same patient;

Step 4: Collecting cytotoxic T lymphocyte and/or NKT cells (induced by the immature dendritic cells) from the same patient;

Step 5: Culturing the cytotoxic T lymphocyte and/or NKT cells collected from the patient;

Step 6: Intratumorally introducing, e.g., injecting, in a therapeutically effective amount of the cultured cytotoxic T lymphocyte and/or NKT cells into the patient. The cytotoxic T lymphocyte cells and NKT cells can be introduced together (e.g., in a mixture or composition) or the cytotoxic T lymphocyte cells can be introduced separately from the NKT cells.

Step 7: Intratumorally introducing, e.g., injecting, in therapeutically effective amount anti-TNF and/or anti-IL-10 into the patient. The anti-TNF and anti-IL-10 can be introduced together (e.g., in a mixture of composition) or introduced separately.

In certain embodiments, Steps 6 and 7 can be combined such that the cultured cytotoxic T lymphocyte and/or NKT cells are combined with the anti-TNF and/or anti-IL-10 in a mixture of composition.

The time allowed to lapse between the above-identified steps can vary. For example, the time between introducing the immature dendritic cells into the patient and introducing the cultured cytotoxic T lymphocyte and/or NKT cells into the same patient can be several hours or days weeks or months. Further, for example, Steps 6 and 7 can be performed within a relatively short period of time or they can be performed concurrently (e.g., simultaneously).

In accordance with Step 5, the culture medium can be selected from those known in the art and can include IL-2, CD3, and mixtures thereof. In certain embodiments, Step 6 can be carried out using an anti-inflammatory agent in addition to the cultured cytotoxic T lymphocyte and/or NKT cells. The cytotoxic T lymphocyte and/or NKT cells and anti-inflammatory agent can be combined to form a composition, and the composition can be intratumorally introduced into the patient. The anti-inflammatory agent can be selected from those known in the art.

As previously described, steps 1, 2 and 3 are prerequisite steps for the inducement of cytotoxic T lymphocyte and/or NKT cells in the patient.

Without intending to be bound by any particular theories, it is believed that cytotoxic T lymphocyte, NKT cells and immature dendritic cells (formed from monocyte cells) which are produced by and collected from a patient provide for an enhanced desired effect when injected into the same patient as compared to cytotoxic T lymphocyte, NKT cells and immature dendritic cells produced and obtained by other means. For example, it appears that the patient's own cytotoxic T lymphocyte, NKT cells which have been collected, cultured and re-introduced intratumorally provide improved coupling or interaction with the cytotoxic T lymphocyte and NKT cells in the body of the patient.

In certain embodiments, the invention provides regression, reduction or elimination of tumor cells in tumor tissue which can be visually detected by MRI and/or CT and/or Echo scan and/or radioisotope.

The invention is more particularly described in the following non-limiting examples, which are intended to be illustrative only, as numerous modifications and variations therein will be apparent to those having skill in the art.

EXAMPLES

Example 1

A MRI was performed on a 71 year-old male patient and the patient was diagnosed with Stage IV prostatic cancer and multiple bone metastasis. The patient had advanced cancer and progressive disease that had not responded to conventional standard therapies. Apheresis was performed on the patient to collect moncyte cells from the patient. The monocyte cells were cultured with IL4 and GM-CFS. This resulted in the production of immature dendritic cells. A cocktail was prepared containing between about $10^7$ to $10^8$ immature dendritic cells and between about 1.0 to 2.0 mg of LCMadj to make up a 10% concentration in normal saline. Depending on the size of the tumor, between 2.0 and 5.0 cc of normal saline was injected into multiple tumor sites of the patient. The patient was also administered radiotherapy and a subsequent intratumoral injection of the cocktail containing the immature dendritic cells and LCMadj.

Apheresis was performed on the patient to collect CTL cells from the patient. The CTL cells were cultured and a cocktail was prepared containing from $10 \times 10^5$ to $30 \times 10^8$ of the cultured CTL cells and 12.5 mg to 50.0 mg of anti-TNF. The cocktail was injected into multiple tumor sites of the patient. The detailed protocol is shown in Table 1.

The patient was evaluated by RI image analysis. Four of the treated tumors of the patient showed complete response (CR), two of the treated tumors showed partial response (PR) and all of the other treated sites showed stable disease (SD). CR is defined as a decrease in serum markers to normal levels and complete disappearance of all measureable lesions. PR is defined as a 30% reduction in the size of the injected tumor, a decline in serum markers, no increase in tumor size at other metastatic sites or appearance of new metastasis. SD is defined as showing less than a 20% increase in tumor size and less than a 30% reduction in tumor size, with no increase in serum tumor markers.

FIG. 1 shows before (e.g., prior to the injection of the CTL and anti-TNF cocktail as described above) and after (e.g., following the injection of the CTL and anti-TNF cocktail as described above) RI images of the lt. rib 7 and 10. These treated tumors were two of the four treated tumors of the patient that showed complete response.

Example 2

A 74 year-old male patient was diagnosed with Stage prostatic cancer and multiple bone metastasis. The patient had advanced cancer and progressive disease that had not responded to conventional standard therapies. Apheresis was performed on the patient to collect moncyte cells from the patient. The monocyte cells were cultured with IL4 and GM-CFS. This resulted in the production of immature dendritic cells. A cocktail was prepared containing between about $10^7$ to $10^8$ immature dendritic cells and between about 1.0 to 2.0 mg of LCMadj to make up a 10% concentration in normal saline. Depending on the size of the tumor, between 2.0 and 5.0 cc of normal saline was injected into multiple tumor sites of the patient. The patient was also administered radiotherapy and a subsequent intratumoral injection of the cocktail containing the immature dendritic cells and LCMadj.

Apheresis was performed on the patient to collect CTL cells from the patient. The CTL cells were cultured and a cocktail was prepared containing $30 \times 10^8$ of the cultured CTL cells and 37.5 mg of anti-TNF. The cocktail was injected into multiple tumor sites of the patient, including sacrum, Th7, Th1.0, Th12, L1, L3, Rt. ilium, Lt. Lt rib 6(1)(2), Lt. rib 10, and Rt. femur. The detailed protocol is shown in Table 2.

The patient was evaluated by RI image analysis. Three of the treated tumors of the patient showed PR (as defined above) and the remaining treated tumors showed CR (as defined above).

Figure 2:
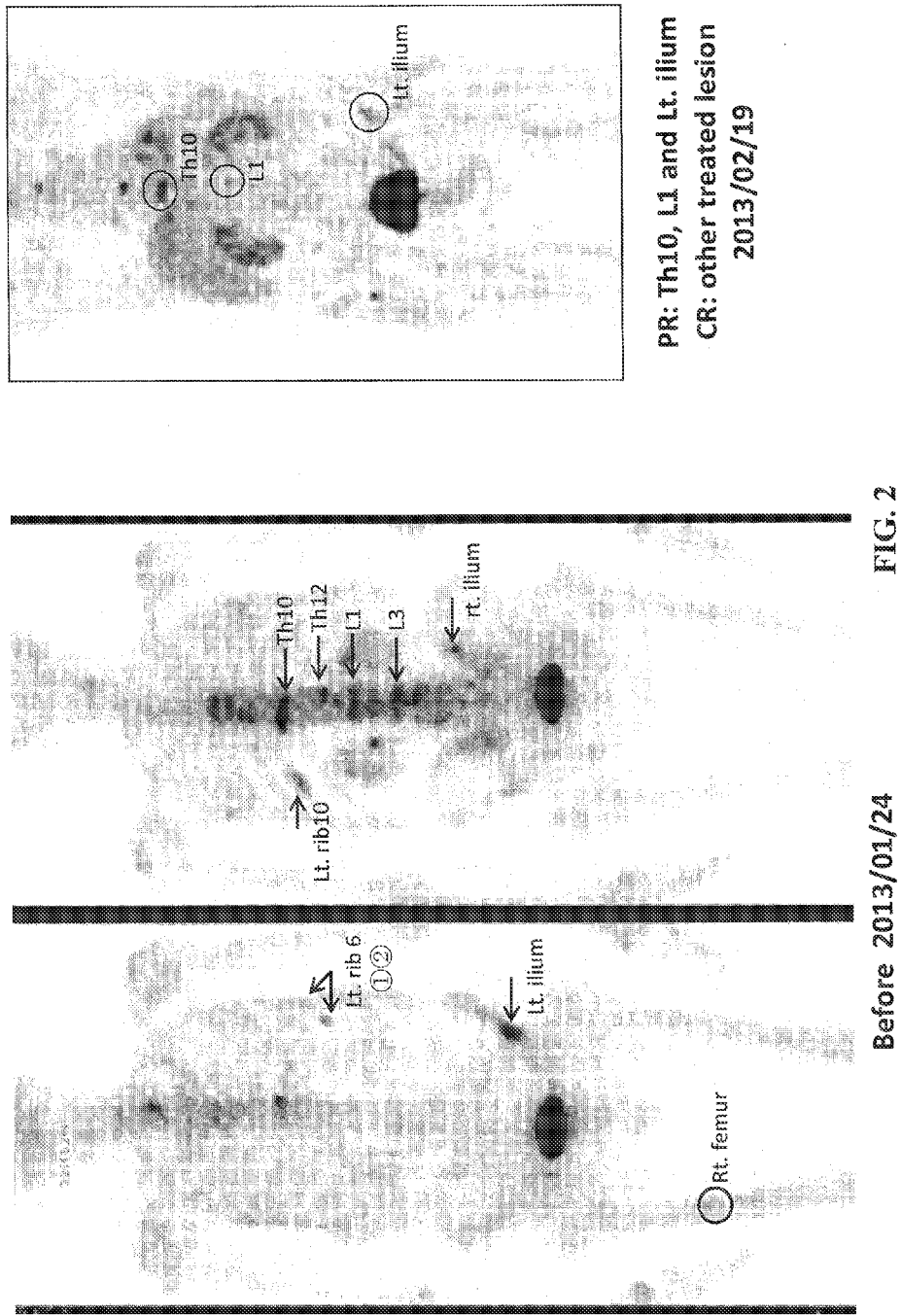
FIG. 2 is a radioisotope image of Th10, L1, lt. ilium, lt. rib 6, Rt. femur, it, rib 10, Th12, L3 and rt. ilium showing tumor tissue before and after therapy, in accordance with one embodiment of this invention.

FIG. 2 shows before (e.g., prior to the injection of the CTL and anti-TNF cocktail as described above) and after (e.g., following the injection of the CTL and anti-TNF cocktail as described above) RI images of the Th10, L1 and Lt. ilium. These treated tumors were the three treated tumors of the patient that showed PR. Further, FIG. 2 shows before RI images of the Lt. rib 6, Rt. femur, Lt. rib 10, Th12, L3 and Rt. ilium. These are the treated tumors that showed CR.

Example 3

A 51 year-old female patient was diagnosed with Stage IV breast cancer and Lt. axilla. LN metastasis. The patient had advanced cancer and progressive disease that had not responded to conventional standard therapies. Apheresis was performed on the patient to collect moncyte cells from the patient. The monocyte cells were cultured with IL4 and GM-CFS. This resulted in the production of immature dendritic cells. A cocktail was prepared containing between about $10^7$ to $10^8$ immature dendritic cells and between about 1.0 to 2.0 mg of LCMadj to make up a 10% concentration in normal saline. Depending on the size of the tumor, between 2.0 and 5.0 cc of normal saline was injected into multiple tumor sites of the patient. The patient was also administered radiotherapy and, subsequent intratumoral injections of immature dendritic cells and LCMadj in combination with 25.0 mg of anti-TNF. The detailed protocol is shown in Table 3.

The patient was evaluated by RI image analysis. The treated tumors of the patient showed PR and CR.

Figure 3:
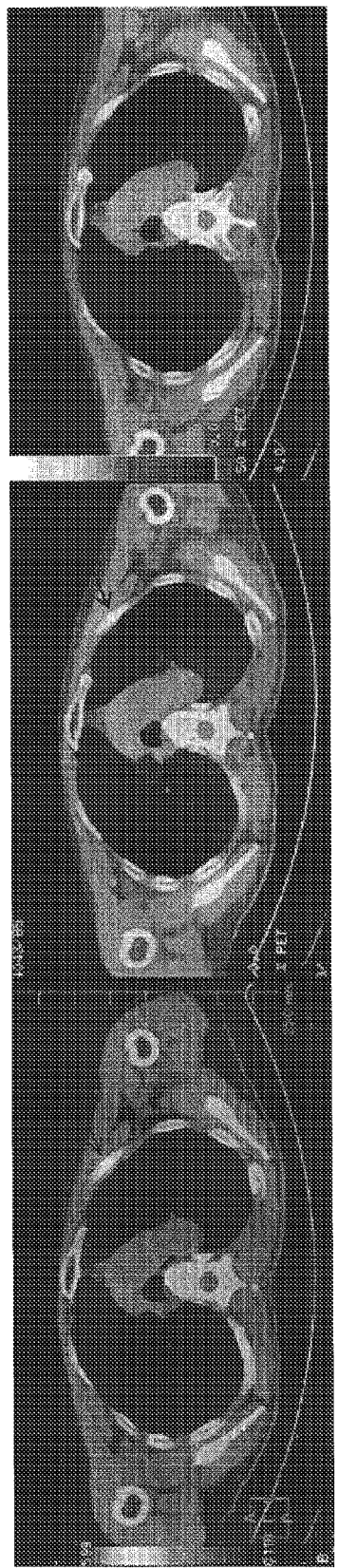
FIG. 3 is a radioisotope image of lt. rib 2 showing tumor tissue before and after therapy, in accordance with one embodiment of this invention.

FIG. 3 shows before and after (PR and CR) RI images of the lt. rib 2.

Example 4

A 79 year-old female patient was diagnosed with Stage II lung cancer and brain metastasis. The patient had advanced cancer and progressive disease that had not responded to conventional standard therapies. Apheresis was performed on the patient to collect moncyte cells from the patient. The monocyte cells were cultured with IL4 and GM-CFS. This resulted in the production of immature dendritic cells. A cocktail was prepared containing between about $10^7$ to $10^8$ immature dendritic cells and between about 1.0 to 2.0 mg of LCMadj to make up a 10% concentration in normal saline. Depending on the size of the tumor, between 2.0 and 5.0 cc of normal saline was injected into multiple tumor sites of the patient. The patient was also administered radiotherapy and a subsequent intratumoral injection of the cocktail containing the immature dendritic cells and LCMadj.

Apheresis was performed on the patient to collect CTL cells from the patient. The CTL cells were cultured and a cocktail was prepared containing from $10 \times 10^8$ to $40 \times 10^8$ of the cultured CTL cells and 12.5 mg to 25.0 mg of anti-TNF. The cocktail was injected into multiple tumor sites of the patient. The detailed protocol is shown in Table 4.

The patient was evaluated by RI image analysis. The treated tumors of the patient showed CR.

Figure 4:
FIG. 4 is a radioisotope image of lt. rib 3 showing tumor tissue before and after therapy, in accordance with one embodiment of this invention.

FIG. 4 shows before and after RI images of the lt. rib 3. This treated tumor showed complete response.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

TABLE 1

Protocol HITV & CTL-II (intra-tumoral)
Prostatic Cancer (Stage IV), Multiple Bone Metastasis
(#0442, 71 Y Male)

| Date | Event |
|---|---|
| 2007/02 | MRI found prostatic cancer, bone metastasis Endocrine therapy: leuplin/casodex |
| 2007/09 | MRI: CR (pancreas), PR (bone meta.) |
| 2008/11 | Rec. |
| 2009/09 | Peptide DC, vitamin C and ozone therapy |
| 2010/01 | MRI: Difuse meta. to the pelvis |
| 2010/02 | IMRT to the prostate gland + pelvis meta. |
| 2010/03 | MRI: mult. bone meta. |
| 2010/03/25 | IMRT: 48.3Gy/20F/21D (primary, SV, bil inguinal LN) 56.2Gy/20F/21D (other bone meta.) |
| 2010/04/04 | Apheresis |
| 2010/04/29 | DC injection to 20 sites |
| 2010/06/01 | DC injection to 30 sites |
| 2010/06/07 | IMRT: 40.0Gy/10Fr/12D |
| 2010/08/06 | MRI: CR (prostate gland) PR (thoracic spine) Rec. (multiple bone) |
| 2010/10/26 | RI: Rec. (multiple bone) |
| 2010/11/15 | IMRT: 26.26Gy/12F/19D (mult. bone meta.) |
| 2010/12/01 | IMRT: 30.00Gy/5Fr/9D (rt. ischium, bil. femur) |
| 2010/12/15 | DC injection to 21 sites |
| 2011/04/21 | RI: PR (lumbar~pelvis) PD (cervical~thoracic) |
| 2011/07/22 | RI: SD (bone meta. overall) |
| 2011/12/09 | CTL apheresis |
| 2011/12/09 | CTL (25.0 × 10*8) w/anti-TNF 25.0 mg(L4/L5) |
| 2012/01/13 | CTL (25.0 × 10*8) w/anti-TNF 25.0 mg (L3/lt.ilium) |
| 2012/02/03 | RI: CR (L4/L3) PR (L5/lt. ilium) Untreated residual tumor (lt. rib 7&10, sternum) |
| 2012/03/28 | CTL (20.0 × 10*8) w/anti-TNF 25.0 mg (lt. rib7&10, sternum) |
| 2012/05/11 | RI: PR (Lt. rib 7&10) SD (sternum) |
| 2012/05/17 | CTL apheresis |
| 2012/06/21 | CTL (10.0 × 10*8) w/anti-TNF 12.5 mg (lt. rib7) |
| 2012/07/19 | CTL apheresis |
| 2012/08/09 | CTL (10.0 × 10*8) w/anti-TNF 12.5 mg (lt.rib10) |
| 2012/08/10 | RI: CR (Lt. rib 10) SD (Lt. rib 7) Rec. (rt. sacrum) |
| 2012/09/03 | CTL (30.0 × 10*8) w/anti-TNF 37.5 mg (stenum/rt.sacrum/lt. ilium) |
| 2012/10/04 | CTL (30.0 × 10*8) w/anti-TNF 37.5 mg (Th7/Th8/Lt.rib7) |
| 2012/11/05 | Apheresis |
| 2012/11/05 | CTL (20.0 × 10*8) w/anti-TNF 50.0 mg (Lt.5/Rt.L5/Th3/Th4) |
| 2012/11/19 | RI: CR (Lt. rib 7) SD (other treated sites) |
| 2012/12/03 | DC w/anti-TNF 50.0 mg to each site (Rt. rib1/sternum) |
| 2013/01/08 | DC w/anti-TNF 50.0 mg to each site (Th3) |
| 2013/02/05 | DC w/anti-TNF 50.0 mg to each site (Lt.L5/Rt.L5) |

TABLE 2

Protocol HITV & CTL-II (intra-tumoral)
Prostatic Cancer (Rec.), Multiple Bone Metastasis
(#0611, 74 Y Male)

| Date | Event |
|---|---|
| 2006/05 | Prostatic cancer (stage III) Brachytherapy |
| 2011/05/12 | Bone scintigram found many bone meta. |
| 2011/05/23 | Apheresis |
| 2011/06/03 | DC injection to 15 bone meta. |
| 2011/06/08 | IMRT: 48.5Gy/10F/14D |
| 2011/06/24 | DC injection |
| 2011/07/22 | Apheresis |
| 2011/08/05 | RI: PR (all treated sites) |
| 2011/09/09 | Weekly CTL div. started |
| 2012/04/16 | RI: SD~PR overall, new lesion at sacrum & th8 |
| 2012/05/30 | Apheresis |
| 2012/05/30 | CTL (30.0 × 10^8) w/anti-TNF 37.5 mg to th7, lt. ilium, sacrum |
| 2013/01/24 | RI: many bone meta. up |
| 2013/02/08 | DC w/anti-TNF 25.0 mg to each site: th10, th12, L1, L3, rt. ilium, lt. ilium, lt. rib 6 1 2, lt. rib 10, and rt. femur |
| 2013/02/19 | PET-CT: PR~CR, new lesion C4 |

TABLE 3

Protocol HITV & CTL-II (intra-tumoral)
Breast Cancer (Stage IV), axilla LN metastasis
(#0675, 51 Y Female)

| Date | Event |
|---|---|
| 2011/10/05 | PET-CT: lt. breast FDG uptake (refused surgery) |
| 2011/10/20 | Biopsy: Invasive ductal carcinoma |
| 2011/10/27 | Apheresis |
| 2011/12/01 | DCAT injection (6 times) |
| 2012/01/07 | Lt. axilla LN up (refused surgery) |
| 2012/01/19 | Apheresis |
| 2012/01/27 | DC injection to lt. breast (4 sites) and lt. axilla LN (3 sites) |
| 2012/02/06 | IMRT: 48.32Gy/20Fr/30D (lt. whole breast) 60.00 Gy/30Fr/30D (Primary + lt. axilla LN) |
| 2012/03/09 | DC injection to lt. breast (2 sites) and lt. axilla LN (4 sites) |
| 2012/04/20 | PET-CT: CR |
| 2012/07/20 | PET-CT: CR |
| 2012/10/27 | PET-CT: CR, but new lesion up (lt. rib 2) |
| 2012/11/09 | DC injection to the lt. rib 2 w/anti-TNF 25.0 mg |
| 2012/11/26 | DC injection w/anti-TNF 25.0 mg |
| 2012/12/27 | PET-CT: PR |
| 2013/02/14 | PET-CT: CR |

TABLE 4

Protocol HITV & CTL-II (intra-tumoral)
Lung Cancer (Stage II), brain metastasis
(#0701, 79 Y Female)

| Date | Event |
|---|---|
| 2011/08 | Tumor enlargement: no surgery because of her weak condition |
| 2011/12/8 | PET-CT: rt. lung primary S3, rt. rib 2, 3, rt. hilar LN |
| 2011/12/28 | Apheresis |
| 2012/01/16 | IMRT: 24.5Gy/5F/5D to primary S3 40.0Gy/5F/5D to ribs |
| 2012/01/24 | DC injection to rt. primary (3 sites), rt. hilar LN, rt. rib 2 & 3 |
| 2012/03/06 | PET-CT: PR (rt. primary), CR (rt. hilar and rt. ribs) New lesion: rt. lung S5, lt. lung S4 and lt. hilar LN |
| 2012/03/14 | Apheresis |
| 2012/04/26 | CTL (40.0 × 10*8) w/anti-TNF 12.5 mg (rt. primary S3, rt. chest cavity) |
| 2012/05/24 | CTL (10.0 × 1.0*8) w/anti-TNF 25.0 mg (lt. hilar LN) |
| 2012/06/06 | PET-CT: PR (primary S3), CR (lt. hilar) and new lesion at lt. rib 6 |
| 2012/06/13 | CTL (10.0 × 10*8) w/anti-TNF 25.0 mg (lt. rib 6) |
| 2012/09/03 | PET-CT: PR (primary S3), CR (lt. rib 6,) no new lesion |
| 2012/09/27 | CTL (10.0 × 10*8) w/anti-TNF 25.0 mg (rt. primary S3, rt. |

TABLE 4-continued

Protocol HITV & CTL-II (intra-tumoral)
Lung Cancer (Stage II), brain metastasis
(#0701, 79 Y Female)

| | |
|---|---|
| | hilar LN) |
| 2012/12/03 | PET-CT: both PR, new lesion at lt. rib 3 |
| 2013/01/22 | DC injection w/anti-TNF 25.0 mg to lt. rib 3 |
| 2013/03/04 | PET-CT: CR |

What is claimed is:

1. A method of regressing, reducing or eliminating tumor cells in tumor tissue of a patient comprising:
   a. collecting monocyte cells from a patient;
   b. culturing the monocyte cells to form immature dendritic cells;
   c. introducing intratumorally a therapeutically effective amount of immature dendritic cells to the patient to generate an immunoresponse and induce cytotoxic T lymphocyte and/or NKT cells;
   d. following step c, collecting cytotoxic T lymphocyte and/or NKT cells from the patient;
   e. following step d, re-introducing intratumorally a therapeutically effective amount of the cytotoxic T lymphocyte and/or NKT cells to the patient; and
   f. introducing intratumorally a therapeutically effective amount of anti-TNF and/or anti-IL-10 to the patient.

2. The method of claim 1, wherein following the collecting in step d, the cytotoxic T lymphocyte and/or NKT cells are cultured.

3. The method of claim 2, wherein the culturing is conducted in a medium comprising IL-2, CD3, and mixtures thereof.

4. The method of claim 1, wherein the re-introducing of the cultured cytotoxic T lymphocyte and/or NKT cells is in conjunction with an anti-inflammatory agent.

5. The method of claim 4, wherein the cultured cytotoxic T lymphocyte and/or NKT cells are combined with the anti-inflammatory agent to form a composition.

6. The method of claim 1, wherein the patient is a human.

7. The method of claim 1, wherein the introducing intratumorally of the anti-TNF and/or anti-IL-10 is carried out prior to the re-introducing intratumorally of the cytotoxic T lymphocyte and/or NKT cells.

8. The method of claim 1, wherein the introducing intratumorally of the anti-TNF and/or anti-IL-10 is carried out following the re-introducing intratumorally of the cytotoxic T lymphocyte and/or NKT cells.

9. The method of claim 1, wherein the introducing intratumorally of the anti-TNF and/or anti-IL-10 is carried out coincidently with the re-introducing intratumorally of the cytotoxic T lymphocyte and/or NKT cells.

10. The method of claim 1, wherein the cytotoxic T lymphocyte is CD8+NK T cell population.

11. The method of claim 1, wherein radiation therapy is excluded.

12. The method of claim 1, wherein the patient is subjected to therapy selected from the group consisting of chemotherapy, radiotherapy, antibody therapy, and combinations thereof.

13. A method of regressing, reducing or eliminating tumor cells in tumor tissue of a patient, comprising:
    a. introducing intratumorally a therapeutically effective amount of immature dendritic cells to the tumor tissue;
    b. collecting cytotoxic T lymphocyte and/or NKT cells from the patient;
    c. culturing the cytotoxic T lymphocyte and/or NKT cells collected from the patient to produce cultured cytotoxic T lymphocyte and/or NKT cells;
    d. combining the cultured cytotoxic T lymphocyte and/or NKT cells with a therapeutically effective amount of anti-TNF and/or anti-IL-10 to form a mixture; and
    e. introducing intratumorally a therapeutically effective amount of the mixture to the patient,
    wherein step a is a prerequisite to steps b, c, d and e.

14. The method of claim 13, further comprising;
    collecting monocyte cells from the patient; and
    culturing the monocyte cells to form the immature dendritic cells.

15. The method of claim 13, wherein the therapeutically effective amount of cytotoxic T lymphocyte and/or NKT cells comprises cytotoxic T lymphocyte and/or NKT cells induced by the introduction of the immature dendritic cells.

* * * * *

UNITED STATES PATENT AND TRADEMARK OFFICE
CERTIFICATE OF CORRECTION

Page 1 of 1

PATENT NO.        : 8,961,957 B2
APPLICATION NO.   : 13/928844
DATED             : February 24, 2015
INVENTOR(S)       : Kenichiro Hasumi It is certified that error appears in the above-identified patent and that said Letters Patent is hereby corrected as shown below:

In the Specification

Column 1, line 37, "Cytotoxic cells" should read --Cytotoxic T cells--.
Column 2, line 39, "it, rib 10" should read --lt. rib 10--.
Column 7, line 53, "Stage pro-" should read --Stage III pro- --.
Column 8, line 6, "Th1.0," should read --Th10,--.
Column 8, line 6, "Lt. Lt rib" should read --Lt. ilium, Lt. rib--.
Column 10, line 19, "lt. rib 6 1 2," should read --lt. rib 6 ① ②,--.

Signed and Sealed this
Seventh Day of July, 2015

Michelle K. Lee
*Director of the United States Patent and Trademark Office*